United States Patent [19]

McCarthy et al.

[11] Patent Number: 5,356,520
[45] Date of Patent: Oct. 18, 1994

[54] SEPARATION OF HIGH BOILING POINT SOLVENTS FROM AMYL ACETATE

[75] Inventors: William Z. McCarthy, St. Louis; Michael J. Gentilcore, Maryland Heights, both of Mo.

[73] Assignee: Mallinckrodt Medical PMC, Las Vegas, Nev.

[21] Appl. No.: 23,283

[22] Filed: Feb. 26, 1993

[51] Int. Cl.$^5$ ............................................. B01D 3/14
[52] U.S. Cl. ............................ 203/81; 203/DIG. 21; 560/248
[58] Field of Search ............... 203/81, 74, DIG. 21; 560/248

[56] References Cited

U.S. PATENT DOCUMENTS

| | | |
|---|---|---|
| 3,084,109 | 4/1963 | Reid et al. ............... 203/7 |
| 3,084,110 | 4/1963 | Polk ............................ 203/7 |
| 3,553,101 | 1/1971 | Foroulis ..................... 203/7 |
| 3,625,886 | 12/1971 | Mattia ...................... 203/92 |
| 3,642,447 | 2/1972 | Hahn et al. ................ 203/12 |
| 4,153,806 | 5/1979 | Peltzman ................... 203/81 |
| 4,690,734 | 9/1987 | Berg et al. ................. 203/64 |

FOREIGN PATENT DOCUMENTS 1202936 8/1970 United Kingdom .................... 203/7

*Primary Examiner*—Virginia Manoharan
*Attorney, Agent, or Firm*—Rita Downard Vacca

[57] ABSTRACT

A process for the separation of amyl acetate, a high boiling point solvent from various high boiling point corrosive impurities, namely, bromoethyl acetate, in an industrial setting to allow for reuse through continuous recycling thereof.

4 Claims, No Drawings

SEPARATION OF HIGH BOILING POINT SOLVENTS FROM AMYL ACETATE

FIELD OF THE INVENTION

This invention relates to a process for the separation of high boiling point solvents from amyl acetate and, more particularly, to the purification of amyl acetate to reduce the level of bromoethyl acetate, dimethylsulfoxide, ethylene glycol monoacetate, ethylene glycol diacetate, and other high boiling solvents therein to allow for continuous industrial recycling reuse thereof.

BACKGROUND OF THE INVENTION

Ioversol was disclosed as a useful nonionic X-ray contrast agent in U.S. Pat. No. 4,396,598. In the synthesis of Ioversol, amyl acetate is used for the crystallization of N,N'-Bis(2,3-dihydroxypropyl)-5-[N-(2-hydroxyethyl) glycolamido]-2,4,6-triiodoisophthalamide hexaacetate (ester) (hereinafter referred to as "hexaacetate") and wash of the hexaacetate filter cake. After the amyl acetate is used for the crystallization and wash steps, the crude amyl acetate or mother liquor contains several impurities. A few of these impurities are 1,1,2-trichloroethane (hereinafter referred to as "TCE"), bromoethyl acetate (hereinafter referred to as "BEA"), dimethylsulfoxide (hereinafter referred to as "DMSO"), ethylene glycol monoacetate (hereinafter referred to as "EGMA") and ethylene glycol diacetate (hereinafter referred to as a "EGDA").

Until this time, the purification process used to recover amyl acetate for reuse was to distill the amyl acetate mother liquor to separate amyl acetate, TCE, BEA, DMSO, EGMA and EGDA from the tars and non-volatile impurities, and then to fractionate the amyl acetate solution to remove the TCE from the amyl acetate solution as a lower boiling point fraction. Following this purification procedure, the higher boiling point amyl acetate solution still contained other high boiling point substances in small quantities, including BEA, EGMA, EGDA and DMSO. These impurities, particularly BEA, are a problem in the purification process of amyl acetate due to a build-up thereof in the amyl acetate after continuous recycling of the amyl acetate in the industrial setting and due to its corrosiveness.

An alternative method of purification for amyl acetate which would eliminate the build-up of BEA and similar such impurities therein is desired. It is an object of the present invention to meet this need.

SUMMARY OF THE INVENTION

In order to purify amyl acetate according to the present invention for reuse through continuous recycling following the crystallization and wash of hexaacetate, the crude amyl acetate solution, or the mother liquor, is distilled to separate the amyl acetate, TCE, BEA, DMSO, EGMA and EGDA away from the tars and non-volatile components. The amyl acetate solution is then fractionated to remove the TCE from the solution as a lower boiling point fraction. The higher boiling point fraction containing amyl acetate, BEA, DMSO, EGMA and EGDA and other high boiling point components is then passed through a second distillation and purification scheme which is unexpectedly capable of separating and purifying the amyl acetate under the highly corrosive conditions created by BEA.

This improved process for the purification of amyl acetate has the advantage of eliminating the build-up of bromoethyl acetate and other high boiling point impurities therein. The elimination of the build-up of bromoethyl acetate in the amyl acetate decreases costs by allowing for the reuse of amyl acetate through continuous recycling in the industrial setting.

DETAILED DESCRIPTION OF THE INVENTION

The unique purification process of the present invention unexpectedly enables amyl acetate, a comparatively expensive solvent used in the synthesis of Ioversol, to be recovered and purified for reuse through continuous industrial recycling.

Amyl acetate is used for the crystallization of hexaacetate and wash of the hexaacetate filter cake in the production of Ioversol. After such use, the crude amyl acetate or mother liquor, contains several impurities, such as but not limited to 1,1,2-trichloroethane (TCE), dimethylsulfoxide (DMSO), ethylene glycol monoacetate (EGMA), ethylene glycol diacetate (EGDA), and bromoethyl acetate (BEA). This mother liquor is distilled to separate the amyl acetate solution containing small quantities of BEA, DMSO, EGMA, EGDA, and TCE, away from the tars and non-volatile components. The solution is then fractionated to remove TCE, i.e., the lower boiling point solution, and possibly also small quantities of water. After the removal of TCE and possibly water, the high boiling point crude amyl acetate solution still contains impurities such as but not limited to BEA, DMSO, EGMA, and EGDA. This crude amyl acetate solution is then fed to a distillation column uniquely designed to separate amyl acetate as a lower boiling point solvent from the higher boiling point impurities, namely BEA, EGMA, EGDA and DMSO. This separation of amyl acetate from BEA, EGMA, EGDA and DMSO eliminates the undesirable build-up of BEA and like impurities in the amyl acetate thus enabling reuse thereof through continuous industrial recycling.

The unique design of the distillation system used to separate amyl acetate from other very high boiling point solvents requires special consideration. Corrosion considerations for continuous industrial use must be addressed since the BEA is highly corrosive. For this reason, the reboiler is preferably fabricated from Hastelloy TM C-276 steel—manufactured by Haynes International, Inc., Karbate TM—a corrosion resistant carbon material manufactured by Karbate Vocarb Inc. or similar such corrosion resistant materials. Hastelloy TM C-276 steel is an ideal material for the reboiler since it is resistant to corrosion by bromoethyl acetate and bromoethyl acetate's decomposition products which may include bromine. Additionally, Hastelloy TM C-276 steel is not as brittle as Karbate TM which reduces the dangers of cracking and increases attendant safety. A second unique material of construction requiring special consideration in designing this purification system is the distillation packing material. Because of the corrosive nature of the vapors emitted from the amyl acetate solution, ceramic packing is the most useful. Corrosion tests have shown that ceramic packing materials are more corrosion resistant and thus are capable of providing a practical lifetime for industrial use under such corrosive conditions. Other normally desirable packing materials such as metallic packing or nonmetallic packing as currently available, are not economical. Metallic packing is currently constructed with a gauge of metal which corrodes very quickly and therefore is not economical. Nonmetallic packings such as Teflon TM manufactured by E. I. duPont de Nemours or polypropylene do not have good wetting characteristics for the present purpose and thereby require taller distillation columns. This option is likewise not industrially economical. However, as technology improves allowing for a more favorable gauge metallic packing or non-metallic packing with more desirable wetting characteristics, these products could prove to be useful.

As various changes could be made in the above unique purification process without departing from the scope of the invention, it is intended that all matter contained in the above description shall be interpreted as illustrative and not in a limiting sense.

What is claimed is:

1. A process for the purification of a crude amyl acetate solution comprising the steps of:

distilling said crude amyl acetate solution to remove tars and non-volatile components, fractionating said crude amyl acetate solution, wherein said tars and non-volatile components have been removed, to remove lower boiling point impurities, and redistilling said crude amyl acetate solution wherein said lower boiling point impurities have been removed whereby purified amyl acetate is separated from higher boiling point impurities including bromoethyl acetate or dimethylsulfoxide.

2. The process of claim 1 wherein said lower boiling point impurities include 1,1,2-trichloroethane.

3. The process of claim 1 wherein said lower boiling point impurities include water.

4. The process of claim 1 wherein said lower boiling point impurities including 1,1,2-trichloroethane and water are removed from said crude amyl acetate by fractionation.

* * * * *